United States Patent [19]

Hirata et al.

[11] 4,316,958

[45] Feb. 23, 1982

[54] PROCESS FOR PRODUCING OPTICALLY ACTIVE CEPHALOSPORIN ANALOGS

[75] Inventors: Tadashi Hirata, Yokohama; Yukio Hashimoto, Yamato; Takehiro Ogasa; Shigeru Kobayashi, both of Machida; Ikuo Matsukuma, Yokkaichi; Kazuo Kimura, Hofu, all of Japan

[73] Assignee: Kyowa Hakko Kogyo Co., Ltd., Tokyo, Japan

[21] Appl. No.: 119,451

[22] Filed: Feb. 7, 1980

[30] Foreign Application Priority Data

Feb. 10, 1979 [JP] Japan .................................. 54-14553
Aug. 24, 1979 [JP] Japan ................................ 54-107070

[51] Int. Cl.³ ............................................ C12P 17/18
[52] U.S. Cl. ...................................... 435/119; 435/51
[58] Field of Search ................................. 435/119, 51

[56] References Cited

U.S. PATENT DOCUMENTS 3,749,641 7/1973 Takahashi et al. .................... 435/51
3,962,036 6/1976 Liersch et al. ........................ 435/51
4,207,395 6/1980 Cassidy et al. ..................... 435/119

OTHER PUBLICATIONS

Guthikonda et al., J. Am. Chem. Soc. vol. 96 pp. 7584–7585 (1974).

*Primary Examiner*—Alvin E. Tanenholtz
*Attorney, Agent, or Firm*—Fitzpatrick, Cella, Harper & Scinto

[57] ABSTRACT

Optically active cephalosporin analogs are produced by optically selective deacylation of an optically inactive acylated analog. The compounds are useful as intermediates in the preparation of optically active acylated antimicrobial agents.

5 Claims, No Drawings

PROCESS FOR PRODUCING OPTICALLY ACTIVE CEPHALOSPORIN ANALOGS

BACKGROUND OF THE INVENTION

The present invention relates to optically active cephalosporin analogs and, more particularly, it pertains to optically active compounds of cephalosporin analogs represented by the general formula (I)

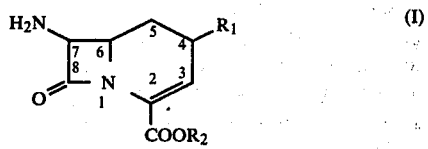

wherein $R_1$ represents a hydrogen or a lower alkyl group, $R_2$ represents a hydrogen or a protective group of carboxylic acid, and the hydrogens at the 6- and 7-positions have cis configuration, the pharmaceutically acceptable salts thereof and processes for producing the same.

Heretofore, a carbacephem compound, which is named according to the nomenclature in J. Am. Chem. Soc. 96, 7584 (1974), wherein the sulfur atom of cephalosporin is substituted with a carbon atom and which has a substituted methyl group at the 3-position is described in the above reference and J. Med. Chem. 20, 551 (1977). However, no compound of this type having especially strong antibacterial activity has been reported.

The present inventors have succeeded in preparing carbacephem compounds having various substituents at the 4-, 5- and 3-positions [The numbering system is as shown in general formula (1)]. The compounds are described in the specifications of Japanese Published Unexamined Patent Application No. 128591/79, German Offenelegungsschrift 2911786, referred as "G.O." hereinafter, and U.S. Pat. Application Ser. No. 23,645 filed on Mar. 23, 1979.

Further, the present inventors have succeeded in preparing novel acylated carbacephems which are new antibiotics having strong antibacterial activities. These are described in Japanese Published Unexamined Patent Application No. 128591/79, G.O. 2911787 and U.S. Pat. Application Ser. No. 23,646 filed on Mar. 23, 1979.

However, cephalosporin analogs mentioned above are prepared by synthetic methods using optically inactive starting compounds, and they are optically inactive dl [represented by (±)] compounds unless they have optically active acyl group. More specifically, compounds represented by the general formula (I) wherein the hydrogen atoms at the 6- and 7-positions have cis configuration are present as a mixture of equal amounts of the mirror image compounds represented by the formulae (I-1) and (I-2)

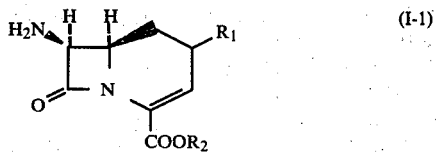

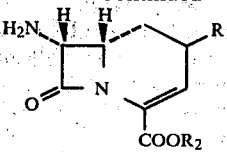

wherein $R_1$ and $R_2$ have the same significance as defined above. However, no method of isolating one of these enantiomers has been reported.

To this end, it has now been found that one of the optically active mirror image compounds can be prepared and isolated.

SUMMARY OF THE INVENTION

In accordance with the present invention, optically active compounds are prepared of cephalosporin analogs represented by the formula:

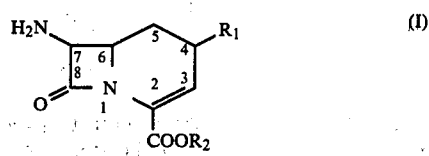

(wherein $R_1$ represents a hydrogen or a lower alkyl group, $R_2$ represents a hydrogen or a protective group of carboxylic acid and the hydrogens at the 6- and 7-positions have cis configuration) and salts thereof.

In the foregoing general formula (I), the lower alkyl group $R_1$ is a straight or branched alkyl group having 1 to 5 carbon atoms such as methyl group, ethyl group, n-propyl group, i-propyl group, n-butyl group, i-butyl group, sec-butyl group, t-butyl group, and the like.

The ester group $COOR_2$ is a group readily convertible to COOH employed in the chemistry of penicillins and cephalosporins.

The group $R_2$, may be a straight-chain or branched alkyl group having 1 to 5 carbon atoms such as methyl group, ethyl group, n-propyl group, i-propyl group, n-butyl group, i-butyl group, sec-butyl group, t-butyl group, and the like; a straight-chain or branched alkoxymethyl group having 1 to 5 carbon atoms such as methoxymethyl group, ethoxymethyl group, and the like; a straight or branched halogenated alkyl group having 1 to 5 carbon atoms such as chloromethyl group, 2,2,2-trichloroethyl group, 2,2,2-trifluoroethyl group, and the like; a lower alkylsulfonylethyl group such as methylsulfonylethyl group, ethylsulfonylethyl group, and the like; an arylmethyl group having 7 to 12 carbon atoms such as benzyl group, diphenylmethyl group, trityl group, triphenylmethyl group, and the like; a substituted arylmethyl group having 7 to 20 carbon atoms wherein the substituent is methoxy group, nitro group, or the like and the number of the substituents on the phenyl ring is 1 to 5; or a protective group of carboxylic acid represented by the general formula (II)

wherein $R_3$ represents a straight-chain or branched lower alkyl group having 1 to 5 carbon atoms, a straight-chain or branched lower alkoxy group having 1 to 5 carbon atoms, or a phenyl group, and $R_4$ represents a hydrogen or a straight-chain or branched lower alkyl group having 1 to 5 carbon atoms.

The optically active compounds of cephalosporin analogs represented by the general formula (I), that is, one of the enantiomers, are prepared, according to the present invention, by an optically selective deacylation reaction using an enzyme and an optically inactive dl compound having an acyl group as a certain starting compound. The desired compound is obtained in a remarkably high yield by this method.

A compound wherein an optically active acyl group is introduced to a dl form of a compound represented by the general formula (I), referred to as Compound (I) hereinafter, that is, the compound represented by the general formula (A)

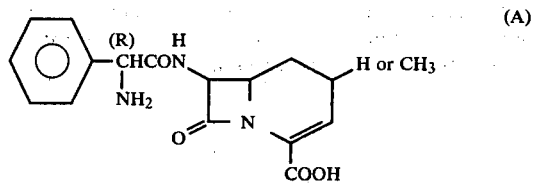

is separated to diastereoisomers (Japanese Published Unexamined Patent Application No. 128591/79, G.O.2911787 and U.S. Pat. Application Ser. No 23646).

The optically active compounds obtained in the present invention are assumed to have the absolute structure represented by the general formula (I-1), that is (6R, 7S), from various properties, strong antimicrobial activity of the acyl compounds as compared with the corresponding optically inactive dl-compound and the relationship between the absolute chemical structure of cephalosporins and activities thereof. These compounds are particularly useful as intermediates in the preparation of optically active acylated compounds which are strong antibacterial agents.

In the following description, the optically active compounds are described with reference to the general formula (I-1). Additionally, the compounds in the following examples and reference examples are named according to the assumed absolute structural formula.

DETAILED DESCRIPTION OF THE INVENTION

Optically active compounds of the cephalosporin analogs represented by the general formula (I) or compounds represented by the assumed absolute structural formula (I-1) are produced by optically selective deacylation of a compound represented by the general formula (III)

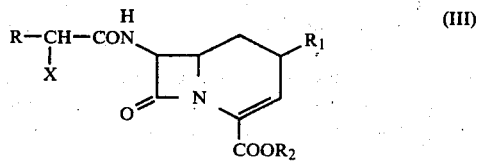

wherein R represents a substituted or unsubstituted unsaturated six-membered carbocyclic or five- or six-membered heterocyclic group, wherein substituent represent hydroxy group, halogens, nitro group or methansulfonamide group, X represents a hydrogen, an amino group, a hydroxy group or a lower alkyl group, $R_1$ and $R_2$ have the same significance as defined above, and the hydrogens at the 6- and 7-positions have cis configuration (referred to as Compound [III] hereinafter).

As the unsaturated six-membered carbocyclic and five-or six-membered heterocyclic group, phenyl group, cyclohexenyl group, cyclohexadienyl group, thienyl group, furyl group pyrrolyl group, thiazolyl group, iso-thiazolyl group, oxazolyl group, iso-oxazolyl group, imidazolyl group, pyrazolyl group, triazolyl group, tetrazolyl group, pyridinyl group, and pyrazinyl group are exemplified. As the substituent, hydroxy group, halogens, nitro group, methanesulfonamide group, and the like are mentioned. As the lower alkyl group, straight-chain or branched alkyl groups having 1 to 5 carbon atoms such as methyl group, ethyl group, n-propyl group, isopropyl group, n-butyl group, i-butyl group, sec-butyl group, t-butyl group and the like are mentioned.

The optically selective deacylation of Compound [III] to obtain optically active Compound [I] is carried out in the presence of an enzyme obtained from a microorganism capable of producing optically active Compound [I] by optically selective deacylation of Compound [III].

As the microorganism having the ability of optically selective deacylation, microorganisms belonging to the genus Aeromonas, Achromobacter, Arthrobacter, Acetobacter, Alcaligenes, Escherichia, Xanthomonas, Kluyvera, Gluconobacter, Clostridium, Comamonas, Corynebacterium, Sarcina, Staphylococcus, Spirillum, Bacillus, Pseudomonas, Flavobacterium, Brevibacterium, Protaminobacter, Proteus, Beneckea, Micrococcus, Mycoplana and Rhodopseudomonas are used. The following strains are examples of the microorganism.

| | |
|---|---|
| Aeromononas hydrophila | IFO 12634 |
| Achromobacter aceris | IFO 3320 |
| Arthrobacter simplex | ATCC 15799 |
| Acetobacter aurantius | IFO 3245, IAM 1812 |
| Acetobacter sp. | ATCC 21760 |
| Alcaligenes faecalis | ATCC 8750 |
| Escherichia coli | ATCC 11105 |
| Escherichia coli | ATCC 13281 |
| Xanthomonas citri | IFO 3835 |
| Xanthomonas physalidicola | IFO 13555 |
| Kluyvera citrophila | ATCC 21285 |
| Gluconobacter liquefaciens | ATCC 14835 |
| Clostridium acetobutylicum | IFO 3346 |
| Comamonas sp. | FERM-P 2410 |
| Corynebacterium tritici | IFO 1216 |
| Sarcina lutea | ATCC 9341 |
| Staphylococcus aureus | IFO 3060 |
| Spirillum methamorphum | IFO 12012 |
| Bacillus megaterium | ATCC 14945 |
| Pseudomonas melanogenum | ATCC 17808 |
| Pseudomonas aeruginosa | IFO 3451 |
| Flavobacterium sp. | ATCC 21429 |
| Brevibacterium cerinum | ATCC 15112 |
| Protaminobacter alboflavus | IFO 13221 |
| Proteus rettgeri | ATCC 9250 |
| Beneckea hyperoptica | ATCC 15803 |
| Micrococcus luteus | AHU 1427 |
| Mycoplana bullata | IFO 13267 |
| Mycoplana dimorpha | IFO 13213 |
| Rhodopseudomonas spheroides | ATCC 21286 |

For carrying out the optically selective deacylation reaction, the enzyme may be provided, more specifically, in any of the following forms:

1. As the culture liquor of the microorganism or treated matter thereof;
2. As cell bodies recovered from the culture broth by centrifugation which may be washed with saline water (usually about 1%), buffer solution and the like, or as a cell suspension;

3. As a disrupted cell suspension, i.e., a suspension of the cell bodies disrupted mechanically or chemically;
4. As a cell free extract, i.e., a liquid obtained by removing the disrupted cell bodies from the disrupted cell suspension; or
5. As a purified enzyme solution which is obtained by recovering the enzyme protein with ammonium sulfate from the cell free extract and subjecting the enzyme protein to gel filtration, ion-exchange cellulose column chromatography, ion-exchange sephadex column chromatography, and the like.

Cells or the purified enzyme immobilized by a conventional method may be used.

The reaction is carried out at a temperature of 0° to 40° C., preferably 15° to 35° C. and at a pH of 5 to 8 in an inactive solvent which does not affect the reaction.

As the solvent, water is most preferably used. In order to dissolve the substitute or cephalosporin analogs, organic solvents such as acetone, methanol, ethanol, N,N-dimethylformamide, dimethylsulfoxide, and the like may be used. It is effective to add phosphate buffer, Veronal buffer or citric acid buffer to control the pH in the reaction. Reaction time being influenced by the kind and concentration of enzymes, the kind and concentration of substrates, reaction temperature or reaction pH, is generally 30 minutes to 24 hours. It is most preferable to terminate the reaction when the reaction ratio reaches maximum.

The concentration of cells is preferably 1 to 50 mg by dry weight per 1 ml of the reaction solution. When a purified enzyme is used, it is appropriate to use the amount of the enzyme having the same activity as that of the dry cell. The substrate Compound [III] is used in an amount of 0.5 to 50 mg per 1 ml of the reaction solution.

In the event the microorganism utilized also produces an enzyme such as β-lactamase, esterase or the like, which tend to prevent the desired reaction, such microorganisms can be mutated by known techniques to obtain a mutant strain which has a reduced productivity of the undesirable enzyme. Alternatively, inhibitors of such enzymes may be added in the reaction system to raise the reaction ratio.

After the completion of the reaction, isolation of the desired compound is carried out by a conventional method employed in the isolation and purification of organic compounds from culture liquors such as absorption using various carriers, ion-exchange chromatography, gel filtration, liquid-liquid extraction, and the like.

Among the compounds represented by the general formula (I), the optically active compounds of the cephalosporin analogs represented by the general formula (I-3)

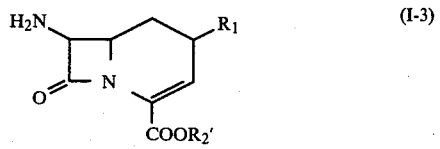

(wherein $R_1$ has the same significance as defined above, $R'_2$ represents a protective group of carboxylic acid and the hydrogens at the 6- and 7-positions have cis configuration) may also be obtained by the esterification of the optically active cephalosporin analogs represented by the general formula (I-4)

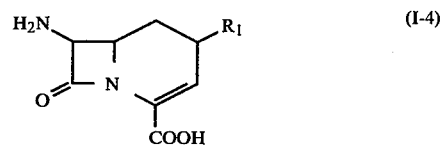

(wherein $R_1$ has the same significance as defined above, and the hydrogens at the 6- and 7-positions have cis configuration) by a conventional method, that is, the compound represented by the formula (I-3')

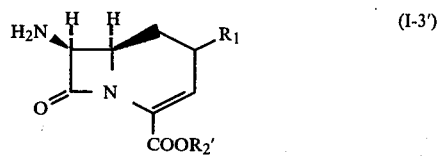

(wherein $R_1$ and $R'_2$ have the same significance as defined above) are obtained by the esterification of the compound represented by the formula (I-4')

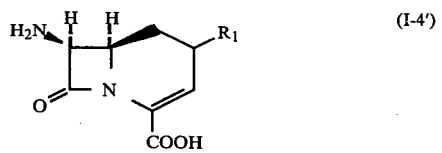

(wherein $R_1$ has the same significance as defined above) by a conventional method.

As the pharmaceutically acceptable salts of the compounds of the invention, salts of the inorganic or organic bases, for example, the alkali metal salts such as sodium salts, potassium salts, etc., alkali earth metal salts such as magnesium salts, etc., ammonium salts, trimethylamine salts, triethylamine salts, pyridine salts, procaine calts, purine salts, lysine salts, arginine salts, etc. and salts of inorganic or organic acid, for example, hydrochloride, sulfate, carbonate, phosphate, formate, trifluoroacetate, malate, etc. are exemplified.

Optically active compounds of the present invention, that is, Compound [I-1], themselves are expected to have antimicrobial activities and the acyl compounds of the optically active Compound [I] (Compound [I-1]) have much stronger antimicrobial activities then the acyl compounds of the corresponding optically inactive Compound [I]. Examples of such compounds and antimicrobial activities thereof are described in Reference Examples.

Certain specific embodiments of the present invention are illustrated by the following representative examples.

EXAMPLE 1

Preparation of (+)-cis-7-amino-1-azabicyclo [4,2,0] oct-2-en-8-on-2-carboxylic acid [(+)-cis-7-amino-2-carboxy-1-azabicyclo [4,2,0] oct-2-en-8-on]: (cis refers to the stereochemistry at the 6- and 7-positions and the same shall apply hereinafter)

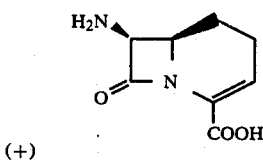

(+)

In this example the following steps are performed.

Cultivation of a microorganism having an ability of optically selective deacylation As the seed strain, *Kluyvera citrophila* ATCC 21285 [Biological properties are described in J. General Applied Microbiology 3, 28–31 (1957)] is used.

As the seed medium, an aqueous solution containing 1% polypeptone, 1% yeast extract, 0.5% meat extract, 0.5% sodium glutamate and 0.25% sodium chloride and adjusted at a pH of 7.0 with 5 N-NaOH is used. One loopful of the seed strain is inoculated into 10 ml of the seed medium in 50 ml of a large test tube and culturing is carried out at a temperature of 30° C. for 24 hours. The whole of the seed broth is inoculated into 300 ml of the culture medium in 2 l of an Erlenmeyer flask and culturing is carried out at a temperature of 30° C. with shaking. The composition of the main culture medium is the same as that of the seed medium.

Preparation of disrupted cell suspension

After culturing for 24 hours, the culture broth is subjected to centrifugation to obtain cell bodies. The cells are then washed twice with 50 ml of 0.9% saline solution and suspended in a concentration of 40 mg/ml by dry weight in 1/30 M phosphate buffer solution. Then, 10 ml of the cell suspension is put into 50 ml large test tube and subjected to ultrasonic disintegration at 200 W for 2 minutes to obtain disrupted cell suspension. In the treatment, an ultrasonic disintegrator Model UR200P (product of Tomy Seiko Co., Ltd.) is used.

Preparation of a substrate solution

In this step, 200 mg of (±)-cis-7-phenylacetamido-1-azabicyclo[4,2,0]oct-2-en-8-on-2-carboxylic acid obtained as in GO 2911787 is added to 9 ml of 1/30 M phosphate buffer (pH 6.5). Since the compound is not dissolved, a small portion of 2N-NaOH is added and the mixture is again adjusted to a pH of 6.5 to dissolve the compound. Finally, deionized water is added to make 10 ml of a solution.

Enzyme reaction

In this step, 10 ml of the disrupted cell suspension mentioned above is added to 10 ml of the substrate solution and enzyme reaction is carried out at a temperature of 30° C. for 80 minutes. Time course of the reaction is illustrated in the following Table 1.

TABLE 1

| Reaction period (minutes) | The amount of Compound [I-1] produced (mg/ml) | Yield (Mol ratio, %) |
|---|---|---|
| 10 | 2.0 | 33 |
| 20 | 2.6 | 43 |
| 40 | 2.9 | 48 |
| 60 | 3.0 | 50 |
| 80 | 3.0 | 50 |

As apparent from the Table 1, the reaction and yield are stationary after the conversion ratio of the mixture of the optically active isomers reaches 50% (mol ratio).

Isolation and Purification of the desired compound

After the completion of the reaction, the microbial cells are removed by centrifugation from the reaction solution. The supernatant is adjusted to a pH of 3.0 with 2 N-hydrochloric acid and charged on a column (2.6 cm diameter, 51 cm height) packed with 270 ml of Diaion HP-10 (product of Mitsubishi Kasei Co., Ltd.). Elution is carried out with deionized water and the eluate is collected in 5 ml fractions. The desired compound is eluted out in the fractions from 280 ml to 315 ml. These fractions are concentrated under reduced pressure, lyophilized and dissolved in a small amount of a mixture of water and methanol (50:50 by volume, the same shall apply hereinafter). The solution is then charged on a column (1.6 cm diameter, 64.5 cm height) packed with 130 ml of Sephadex LH-20 (Farmacia Fine Chemicals Inc.). Elution is carried out with a mixture of water and methanol (50:50). The eluate is collected in 5 ml of fractions, and the fractions from 65 ml to 85 ml are combined and concentrated under reduced pressure to remove methanol. Then, the residue is lyophilized to obtain 48 mg of a white powder having the following properties.

IR(KBr)$\nu_{max}^{cm-1}$: 1800, 1790, 1775, 1640, 1620

NMR(100 M D$_2$O-DSS)$\delta$: 6.46(1H, dd, J=3.5, 4.7 Hz), 4.88(1H, d, J=5.2 Hz), 4.06(1H, m), 2.5-1.5(4H, m)

It is determined that the compound has one mole of hydrochloric acid and water. The properties of the compound coincide well with those of the corresponding dl-compound. The value of optical rotation is $[\alpha]_D^{15°} = +48°$ [c=0.5, in 1 M phosphate buffer solution (pH 7.0)] which coincides well with the value in Example 2 below, $[\alpha]_D^{15°} = 48.5°$ [c=0.5, in 1 M phosphate buffer solution (pH 7.0)].

The compound shows a ninhydrin positive single spot at an Rf value of 0.22 on silica gel thin layer chromatography [thin layer plate Merck Art 5721 (product of E. Merck & Co.), solvent for development, isopropanol: acetic acid: water=4:1:1]. The Rf value coincides with that of the optically inactive dl-compound.

EXAMPLE 2

Preparation of (+)-cis-7-amino-1-azabicyclo[4,2,-0]oct-2-en-8-on-2-carboxylic acid (Alternative method)

Preparation of disrupted cell suspension

The same procedure as in Example 1 is repeated.

Preparation of a substrate solution

In this step, 100 mg (+)-cis-7-[(R)-2-phenyl-2-aminoacetamido]-1-azabicyclo[4,2,0]oct-2-en-8-on-2-carboxylic acid obtained as in GO 2911787 is dissolved in 5 ml of 1/30 M phosphate buffer solution (pH 6.5).

Enzyme reaction

In this step, 5 ml of the disrupted cell suspension mentioned above is added to 5 ml of the substrate solution and the enzyme reaction is carried out at 30° C. for 24 hours.

Isolation and Purification

In this step, 46 mg of a white powder is obtained by a similar method as in Example 1. The properties of the compound coincide well with those of the compound obtained in Example 1.

$[\alpha]_D^{15°} = 48.5°$ [c=0.5, in 1 M phosphate buffer solution (pH 7.0)]

EXAMPLE 3

Preparation of (−)-cis-7β-amino-4α-methyl-1-azabicyclo[4,2,0]oct-2-en-8-on-2-carboxylic acid Preparation of disrupted cell suspension A similar procedure as in Example 1 is repeated.

Preparation of a substrate solution

A similar procedure as in Example 1 is repeated except that (±)-cis-7β-phenylacetamido-4α-methyl-1-azabicyclo[4,2,0]oct-2-en-8-on-2-carboxylic acid obtained as in GO 2911787 is used.

Enzyme reaction

A similar procedure as in Example 1 is repeated except that the disrupted cell suspension and the substrate solution obtained in the above are used. The reaction ratio becomes stationary in one hour. The reaction is continued for additional 120 minutes. The yield is 50% (mol ratio) of the (±) substrate.

Isolation and Purification

After the completion of reaction, the microbial cells are removed by centrifugation from the reaction solution. The supernatant is then charged on a column (2.5 cm diameter, 46 cm height) packed with 220 ml of Diaion HP-10. Elution is carried out with deionized water and the eluate is collected in 5 ml fractions. The desired compound is eluted in the fractions from 200 ml to 270 ml. These fractions are concentrated under reduced pressure, lyophilized, and dissolved in a small amount of water and methanol (50:50). The solution is then charged on a column (1.6 cm diameter, 64.5 cm height) packed with 130 ml of Sephadex LH-20 and elution is carried out with a mixture of water and methanol (50:50). The eluate is collected in 5 ml fractions. The fractions from 65 ml to 80 ml are combined and concentrated to remove methanol. Then, the residue is lyophilized to obtain 30.5 mg of a white powder having the following properties.

IR(KBr)$\nu_{max}^{cm-1}$: 1800, 1770(sh), 1760(sh), 1740, 1680, 1630

NMR(100 M D$_2$O-DSS)δ: 6.16(1H, d, J=5.1 Hz), 4.52(1H, d, J=4.9 Hz), 3.86(1H, m), 2.64(1H, m), 1.9-1.4(2H, m), 1.10(3H, d, J=7.3 Hz)

It is determined that the compound is a potassium salt having 2 moles of water. The properties above coincide well with those of the corresponding dl-compound. The compound shows a ninhydrin positive single spot at Rf=0.33 on a silica gel thin layer chromatography (the same silica gel as in Example 1 is used). The Rf value coincides with that of the optically inactive dl-compound.

Optical rotation $[\alpha]_D^{15°} = -30°$ (c=0.5, in 1 M phosphate buffer solution). The value coincides well with that in Example 4, $[\alpha]_D^{15°} = -30.8°$ [c=0.5, in 1 M phosphate buffer solution (pH 7.0)].

EXAMPLE 4

Preparation of (−)-cis-7β-amino-4α-methyl-1-azabicyclo[4,2,0]oct-2-en-8-on-2-carboxylic acid (Alternative method)

Preparation of disrupted cell suspension

A similar procedure as in Example 3 is repeated.

Preparation of a substrate solution

In this step, 100 mg of (+)-cis-7β-[(R)-2-phenyl-2-aminoacetamido]4α-methyl-1-azabicyclo[4,2,0]oct-2-en-8-on-2-carboxylic acid obtained as in G.O. 2911787 is dissolved in 5 ml of 1/30 M phospate buffer solution (pH 6.5).

Enzyme reaction

As in Example 1, 5 ml of the disrupted cell suspension described above is added to 5 ml of the substrate solution and enzyme reaction is carried out at a temperature of 30° C. for 24 hours.

Isolation and Purification

A similar procedure as in Example 3 is repeated to obtain 55 mg of a white powder. The properties of the compound coincide well with those in Example 3.

Optical rotation $[\alpha]_D^{15°} = -30.8°$ [c=0.5, in 1 M phosphate buffer solution (pH 7.0)].

EXAMPLE 5

Preparation of (+)-cis-7-amino-1-azabicyclo[4,2,0]oct-2-en-8-on-2-carboxylic acid (Alternative method):

Cultivation of microorganisms

As the seed microorganism, the following strains are used.

| | |
|---|---|
| Aeromononas hydrophila | IFO 12634 |
| Achromobacter aceris | IFO 3320 |
| Arthrobacter simplex | ATCC 15799 |
| Acetobacter aurantius | IFO 3245 |
| Acetobacter sp. | ATCC 21760 |
| Alcaligenes faecalis | ATCC 8750 |
| Escherichia coli | ATCC 11105 |
| Escherichia coli | ATCC 13281 |
| Xanthomonas citri | IFO 3835 |
| Xanthomonas physalidicola | IFO 13555 |
| Gluconobacter liquefaciens | ATCC 14835 |
| Gluconobacter dioxyacetonicus | IFO 3271 |
| Comamonas terrigena | IFO 12685 |
| Corynebacterium tritici | IFO 1216 |
| Sarcina lutia | ATCC 9341 |
| Staphylococcus aureus | IFO 3060 |
| Spirillum methanorphum | IFO 12012 |
| Bacillus megaterium | ATCC 14945 |
| Pseudomonas melanogenum | ATCC 17808 |
| Pseudomonas aeruginosa | IFO 3451 |
| Flavobacterium sp. | ATCC 21429 |
| Brevibacterium cerinum | ATCC 15112 |
| Protaminobacter alboflavus | IFO 13221 |
| Proteus rettgeri | ATCC 9250 |
| Benecke a hyperoptica | ATCC 15803 |
| Mycoplana bullata | IFO 13267 |
| Mycoplana dimorpha | IFO 13213 |
| Rhodopseudomonas spheroides | ATCC 21286 |

As a medium, an aqueous solution containing 1% meat extract, 1% peptone, 0.3% sodium chloride and 0.5% yeast extract and adjusted at a pH of 7.2 with 5 N-NaOH is used. One loopful seed strain is inoculated into 30 ml of the seed medium in 300 ml of an Erlenmeyer flask and culturing is carried out at a temperature of 30° C. for 24 hours. Cell bodies obtained by centrifugation from the culture broth are washed with 5 ml of 0.9% saline solution and again recovered by centrifugation therefrom. The cell is suspended in 1/30 M phosphate buffer (pH 7.0) in a concentration of 20 mg/ml for dry weight.

Preparation of a substrate solution 150 mg of (±)-cis-7-[(R)-2-phenyl-2-aminoacetamido]-1-azabicyclo[4,2,0]oct-2-en-8-on-2-carboxylic acid prepared as in GO 2911787 is dissolved in 15 ml of 1/30 M phosphate buffer (pH 7.0).

Enzyme reaction 0.5 ml of each cell suspension and 0.5 ml of the substrate solution prepared as in the above are mixed and the mixture is allowed to react at temperature of 30° for 20 hours.

Identification of the product

It is possible to assay diastereoisomers of (±)-cis-7-[(R)-2-phenyl-2-aminoacetamido]-1-azabicyclo[4,2,-0]oct-2-en-8-on-2-carboxylic acid by high speed liquid chromatography as described in GO 2911787. In this Example, diastereoisomer is quantitatively determined by such method. Quantitative determination of 7-amino-1-azabicyclo[4,2,0]oct-2-en-8-on-2-carboxylic acid produced in the above is possible in the same manner.

As apparent from Table 2, in the reaction solution, a more polar diastereoisomer, i.e., (−)-cis-7-[(R)-2-phenyl-2-aminoacetamido]-1-azabicyclo[4,2,0]oct-2-en-8-on-2-carboxylic acid is remained unchanged and a less polar isomer, i.e., (+)-cis-7-[(R)-2-phenyl-2-aminoacetamido]-1-azabicyclo[4,2,0]oct-2-en-8-on-2-carboxylic acid is decreased. Corresponding to the decrease, a peak of (+)-cis-7-amino-1-azabicyclo[4,2,-0]oct-2-en-8-on-2-carboxylic acid is formed. The unbalance of the decrease of (+)-cis-7-[(R)-2-phenyl-2-aminoacetamido]-1-azabicyclo[4,2,0]oct-2-en-8-on-2-carboxylic acid and the formation of (+)-cis-7-amino-1-azabicyclo[4,2,0]oct-2-en-8-on-2-carboxylic acid depends on the presence of β-lactamase in the reaction system.

Enzymes of all microorganisms in Table 2 have an ability of producing optically active compound having the absolute configuration (6R, 7S) by selectively deacylating cephalosporin analogs.

TABLE 2

| Microorganism | The amount of* (+) produced. (mg) 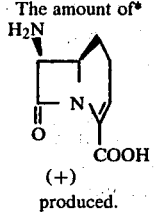 | The amount of** (+) decreased. (mg) 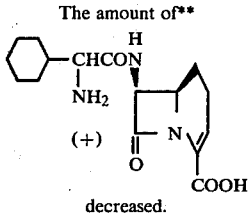 | The amount of (−) decreased. (mg) 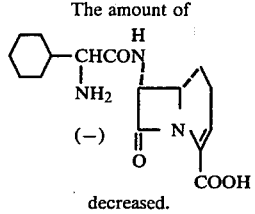 |
|---|---|---|---|
| *Aeromonas hydrophila* IFO 12634 | 0.2 | 2.3 | 0 |
| *Achromobacter aceris* IFO 3320 | 0.4 | 2.0 | 0 |
| *Arthrobacter simplex* ATCC 15799 | 0.2 | 0.8 | 0 |
| *Acetobacter aurantius* IFO 3245 | 0.3 | 1.1 | 0 |
| *Acetobacter* sp. ATCC 21760 | 0.3 | 2.5 | 0 |
| *Alcaligenes faecalis* ATCC 8750 | 0.4 | 1.1 | 0 |
| *Escherichia coli* ATCC 11105 | 0.5 | 1.5 | 0 |
| *Escherichia coli* ATCC 13281 | 0.3 | 1.0 | 0 |
| *Xanthomonas citri* IFO 3835 | 0.9 | 2.5 | 0 |
| *Xanthomonas physalidicola* IFO 13555 | 1.3 | 2.5 | 0 |
| *Beneckea hyperoptica* ATCC 15803 | 1.1 | 2.4 | 0 |
| *Gluconobacter liquefaciens* ATCC 14835 | 0.8 | 2.4 | 0 |
| *Gluconobacter dioxyacetonicus* IFO 3271 | 1.2 | 2.4 | 0 |
| *Comamonas terrigena* IFO 12685 | 0.1 | 0.3 | 0 |
| *Corynebacterium tritici* IFO 1216 | 0.2 | 0.4 | 0 |
| *Sarcina lutea* ATCC 9341 | 0.1 | 0.3 | 0 |
| *Staphylococcus aureus* IFO 3060 | 0.1 | 0.3 | 0 |
| *Spirillum methamorphum* IFO 12012 | 0.2 | 1.0 | 0 |
| *Bacillus megaterium* ATCC 14945 | 0.1 | 0.8 | 0 |
| *Pseudomonas melanogenum* ATCC 17808 | 1.3 | 2.5 | 0 |
| *Pseudomonas aeruginosa* IFO 3451 | 0.5 | 1.1 | 0 |
| *Flavobacterium* sp. ATCC 21429 | 0.5 | 1.5 | 0 |
| *Brevibacterium cerinum* ATCC 15112 | 0.4 | 0.8 | 0 |
| *Protaminobacter alboflavus* IFO 13221 | 1.2 | 2.5 | 0 |
| *Proteus rettgeri* ATCC 9250 | 0.1 | 0.2 | 0 |
| *Mycoplana bullata* IFO 13267 | 1.0 | 2.5 | 0 |
| *Mycoplana dimorpha* IFO 13213 | 1.3 | 2.5 | 0 |
| *Rhodopseudomonas spheroides* ATCC 21286 | 0.3 | 0.6 | 0 |

*When the yield is 100%, 1.4 mg of the compound is produced.
**The initial concentration is 2.5 mg.

EXAMPLE 6

Preparation of (+)-cis-7-amino-1-azabicyclo[4,2,-0]oct-2-en-8-on-2-carboxylic acid (Alternative method):

*Clostridium acetobutylicum* IFO 3346 is inoculated in 100 ml of Potato Dextrose Broth (product of DIFCO Lab.). Air in the fermentor is replaced with sterilized nitrogen gas and the fermentor is sealed. Culturing is carried out at a temperature of 30° C. for 48 hours. After the cultivation, cells are recovered, washed with physiological saline solution and suspended in 2 ml of 1/30 M potassium phosphate buffer (pH 7.0). 0.5 ml of the substrate solution prepared as in Example 5 and the cell suspension are combined and allowed to react at a temperature of 30° C. for 20 hours. The reaction is monitored as in Example 5. (−)-cis-7-[(R)-2-phenyl-2-aminoacetamido]-1-azabicyclo[4,2,0]oct-2-en-8-on-2-carboxylic acid is remained unchanged and only (+)-cis-7-[(R)-2-phenyl-2-aminoacetamido]-1-azabicyclo[4,2,0]oct-2-en-8-on-2-carboxylic acid is decreased. The amount of the decrease is 1.0 mg, producing 0.2 mg of (+)-7-amino-1-azabicyclo[4,2,0]oct-2-en-8-on-2-carboxylic acid.

REFERENCE EXAMPLE 1

Preparation of (+)-cis-7-[2-(2-amino-4-thiazolyl)-2-syn-methoxyiminoacetamido]-1-azabicyclo[4,2,0]oct-2-en-8-on-2-carboxylic acid:

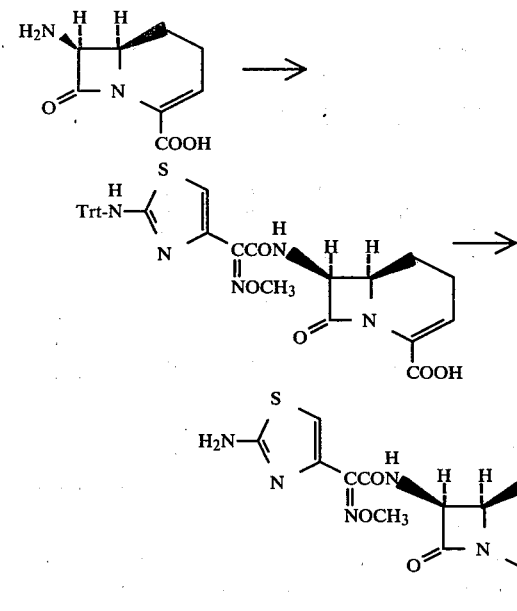

In this Example, 131.3 mg (0.30 m mole) of 2-(2-tritylamino-4-thiazolyl)-2-syn-methoxyiminoacetic acid is dissolved in 1 ml of anhydrous dichloromethane and 4.1 μl of triethylamine is added at a temperature of −20° C. Then, after adding 61.7 mg of phosphorus pentachloride, the mixture is allowed to react at a temperature of −20° C. for 30 minutes and concentrated under reduced pressure. The residue is dissolved in 1 ml of anhydrous tetrahydrofuran to make an acid chloride solution.

Separately, 40.2 mg (0.17 m mole) of the monohydrate of the hydrochloride of (+)-cis-7-amino-1-azabicyclo[4,2,0]oct-2-en-8-on-2-carboxylic acid obtained as in Example 1 is dissolved in a mixture of 1 ml of tetrahydrofuran and 1 ml of water and 116.2 μl of triethylamine is added. The acid chloride solution prepared above is added dropwise to the solution with stirring under ice cooling and the mixture is allowed to react for one hour. Then, the mixture is adjusted to a pH of 2.0 with 5% hydrochloric acid and extracted 3 times with 10 ml of ethyl acetate. The ethyl acetate layers are washed with 10 ml of saturated saline solution, dried with saturated sodium sulfate and concentrated under reduced pressure to obtain 93 mg of a crude acyl compound. The product is dissolved in 10 ml of 50% acetic acid and stirred at a temperature of 50° C. for 1.5 hours. The solution is cooled to room temperature and a deposited white precipitate is removed by filtration. The filtrate is concentrated and the residue is dissolved in a small amount of dimethylsulfoxide. The solution is then charged on a column packed with 10 ml of HP-10 and elution is carried out with water to a mixture of water and methanol (1:2). Fractions showing an Rf value of 0.3 by silica gel thin layer chromatography [plate:- Merck Art. 5719 (product of E. Merck & Co.), solvent- :butanol:acetic acid:water=4:1:1] are combined and concentrated under reduced pressure to obtain 13.5 mg (yield 22.4%) as white crystals having the following properties.

M.P.: 172° C. (dec.)
$[α]_D^{15°} = +32.6°$ (DMSO, c=0.5)
IR(KBr)$ν_{max}^{cm-1}$: 1765, 1660, 1630, 1545
PMR(DMSO-d$_6$)δ: 9.26(1H,d), 7.19(2H,s), 6.75(1H,s), 6.28(1H,t), 5.50(1H,d-d, J=8.9, 4.7 Hz), 3.83(3H,s), 2.5–1.0(4H,m).

These values coincide well with those of the corresponding dl-compound. From the strong antimicrobial activity, absolute configuration of this compound is assumed to be (6R,7S).

REFERENCE EXAMPLE 2

Preparation of (−)-cis-7β-[2-(2-amino-4-thiazolyl)-2-syn-methoxyiminoacetamido]-4α-methyl-1-azabicyclo[4,2,0]oct-2-en-8-on-2-carboxylic acid:

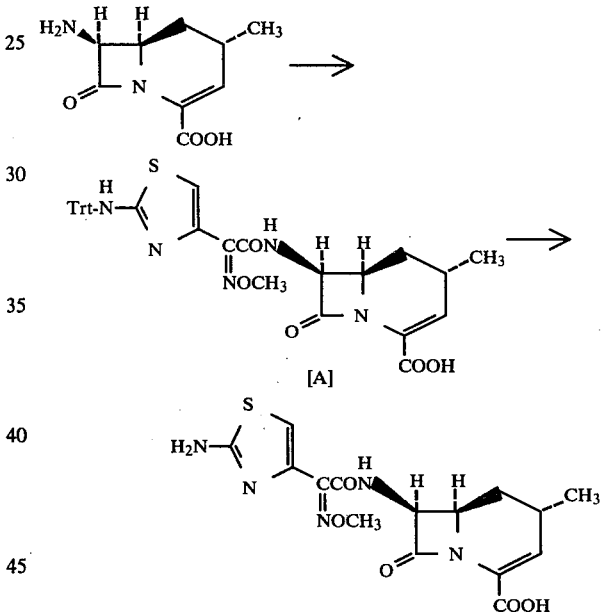

In this Example, 76 mg (0.17 m mole) of 2-(2-tritylamino-4-thiazolyl)-2-syn-methoxyiminoacetic acid is dissolved in 1.52 ml of anhydrous dichloromethane and 17.3 mg (0.17 m mole) of triethylamine is added at a temperature of −15° C. Then after adding 35.7 mg (0.17 m mole) of phosphorus pentachloride, the mixture is allowed to react with stirring at a temperature of −15° C. for 30 minutes. The reaction mixture is concentrated under reduced pressure and the residue is dissolved in 2 ml of anhydrous tetrahydrofuran to make an acid chloride solution.

Separately, 28 mg (0.10 m mole) of the dihydrate of the potassium salt of (−)-cis-7β-amino-4α-methyl-1-azabicyclo[4,2,0]oct-2-en-8-on-2-carboxylic acid obtained as in Example 3 is dissolved in 1.5 ml of a mixture of tetrahydrofuran and water (1:1) and 36.3 mg (0.36 m mole) of triethylamine is added to make a homogeneous solution. To the solution, the acid chloride solution is added dropwise with stirring under ice cooling and the mixture is allowed to react for 45 minutes. Then, the reaction mixture is extracted four times with 3 ml of ethyl acetate. The ethyl acetate layer is washed with 5 ml of saturated saline solution, dried with saturated sodium sulfate, and concentrated under reduced pressure to obtain 107.1 mg of a crude acyl compound represented by the formula [A]. The product is then dissolved in 4.5 ml of 50% acetic acid and the solution is stirred at a temperature of 50° to 55° C. for 45 minutes. After cooling to room temperature, the reaction solution is subjected to filtration to remove a deposited white precipitate and the cake is washed with 2 ml of

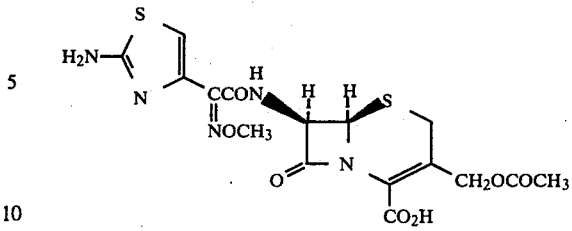

| Microorganism | MIC (μg/ml) | | | | |
| --- | --- | --- | --- | --- | --- |
| | A | A' | B | B' | C |
| *Staphylococcus aureus* 209-P | 3.12 | 12.5 | 1.56 | 6.25 | 0.78 |
| *Staphylococcus aureus* Smith | 6.25 | 25 | 6.25 | 12.5 | 1.56 |
| *Staphylococcus epidermidis* | 12.5 | 25 | 3.12 | 12.5 | 1.56 |
| *Escherichia coli* NIHJC-2 | 0.02 | 0.05 | 0.02 | 0.05 | 0.1 |
| *Escherichia coli* GN2411-5 | 0.01 | 0.05 | ≦0.01 | 0.02 | 0.05 |
| *Escherichia coli* Juhl | 0.02 | 0.1 | 0.02 | 0.05 | 0.05 |
| *Klebsiella pneumoniae* 8045 | ≦0.006 | ≦0.006 | ≦0.01 | 0.01 | ≦0.01 |
| *Klebsiella pneumoniae* Y-60 | 0.02 | 0.05 | 0.02 | 0.05 | 0.05 |
| *Serratia marcescens* T-26 | 0.2 | 0.78 | 0.4 | 0.78 | 0.78 |
| *Serratia marcescens* T-55 | 0.02 | 0.1 | 0.05 | 0.2 | 0.1 |
| *Proteus mirabilis* 1287 | 0.01 | 0.02 | ≦0.01 | 0.01 | 0.02 |
| *Proteus vulgaris* 6897 | ≦0.006 | 0.01 | ≦0.01 | 0.01 | ≦0.01 |
| *Proteus morganii* KY 4298 | 0.05 | 0.1 | 0.02 | 0.1 | 0.05 |
| *Proteus rettgeri* KY 4289 | ≦0.006 | ≦0.006 | ≦0.01 | 0.01 | ≦0.01 |
| *Pseudomonas aeruginosa* #1 | 6.25 | 25 | 25 | 50 | 6.25 |
| *Pseudomonas aeruginosa* 145 | 50 | 50 | 100 | >100 | 50 |
| *Pseudomonas putida* 264 | 0.1 | 0.4 | 0.05 | 0.2 | 0.1 |

50% acetic acid. The washing and filtrate are combined and concentrated under reduced pressure. The residue is dissolved in a small amount of dimethylsulfoxide and charged on a column packed with 10 ml of HP-10. Elution is carried out with water and methanol (5:1 to 2:1). Fractions showing an Rf value at 0.54 by silica gel thin layer chromatography using the same conditions as above, are combined and concentrated under reduced pressure to obtain 12.9 mg (yield 23.8%) of the desired product as a white powder having the following properties.

M.P.: decompose at about 180° C.
$[\alpha]_D^{15°} = -27°$ (DMSO, c=0.5)
IR(KBr)$\nu_{max}^{cm-1}$: 1770, 1672, 1633, 1540
PMR(DMSO-$d_6$)δ: 9.26(1H,d,J=8.3 Hz), 7.18(2H,s), 6.75(1H,s), 6.31(1H,d,J=5.1 Hz), 5.51(1H,d-d,J=8.3, 5.0 Hz), 3.83(3H,s), 1.67(2H,m), 1.07(3H,d,J=7.3 Hz).
The values coincide well with those of the corresponding dl-compound. From the strong antimicrobial activity, absolute configuration of this compound is assumed to be (4S,6R,7S).

REFERENCE EXAMPLE 3

Antimicrobial activities of the compounds obtained in Reference Examples 1 and 2 are as follows. Heart Infusion Agar Dilution Method (pH 7.2) is used. A cephalosporin compound having the same acyl side chain corresponding to the dl-compound is used as a control. The compounds are identified as follows.
A: The compound obtained in Reference Example 1.
A': The dl-compound corresponding to the compound obtained in Reference Example 1.
B: The compound obtained in Reference Example 2.
B': The dl-compound corresponding to the compound obtained in Reference Example 2.
C: Cephalosporin compound represented by the following formula.

What is claimed is:
1. A process for producing an optically active compound represented by the general formula (I)

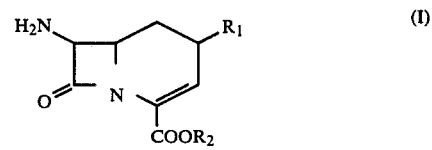

wherein $R_1$ represents a hydrogen or a lower alkyl group, $R_2$ represents a hydrogen or a protective group of carboxylic acid, and the hydrogens at the 6- and 7-positions have a cis configuration, which comprises reacting an optically inactive dl-compound represented by the formula (III)

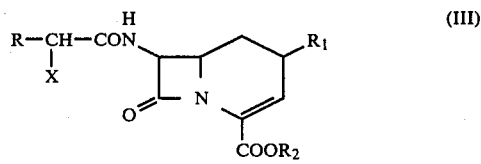

wherein R represents a substituted or unsubstituted unsaturated six-membered carbocyclic or five- or six-membered heterocyclic group, wherein said substituent is a hydroxy group, halogens, a nitro group or a methanesulfonamide group, X represents a hydrogen atom, an amino group, a hydroxy group or a lower alkyl group, $R_1$ and $R_2$ have the same significance as defined above, and the hydrogens at the 6- and 7-positions have a cis configuration, with an enzyme capable of optically selective deacylation and obtainable from a microorganism to optically selectively eliminate the acyl group at the 7-position of the compound represented by the formula III, and thereafter recovering said optically active compound.

2. The process according to claim 1 wherein said enzyme is obtained from a microorganism belonging to the genus Aeromonas, Achromobacter, Arthrobacter, Acetobacter, Alcaligenes, Escherichia, Xanthomonas, Kluyvera, Gluconobacter, Clostridium, Comamonas, Corynebacterium, Sarcina, Staphylococcus, Spirillum, Bacillus, Pseudomonas, Flavobacterium, Brevibacterium, Protaminobacter, Proteus, Beneckea, Micrococcus, Mycoplana or Rhodopseudomonas.

3. The process according to claim 2 wherein said enzyme is provided to said reaction in the form of a purified enzyme solution, cell bodies recovered from a culture broth, a cell suspension, a disrupted cell suspension, a cell free extract, or a culture liquor of the microorganism.

4. The process according to claim 1, wherein said unsaturated six-membered carbocyclic or five- or six-membered heterocyclic group is a member selected from the group consisting of a phenyl group, a cyclohexenyl group, a cyclohexadienyl group, a thienyl group, a furyl group, a pyrrolyl group, a thiazolyl group, an iso-thiazolyl group, an oxadolyl group, an iso-oxazolyl group, an imidazolyl group, a pyrazolyl group, a triazolyl group, a tetrazolyl group, a pyridinyl group and a pyrazinyl group.

5. The process according to claim 1, wherein the reaction is carried out at a temperature of from 0° to 40° C., at a pH of from 5 to 8 and in an inactive solvent.

* * * * *